United States Patent
Aklog et al.

(10) Patent No.: US 11,511,081 B2
(45) Date of Patent: Nov. 29, 2022

(54) SELF-ANCHORING CATHETERS AND METHODS OF USE

(71) Applicant: PAVmed Inc., New York, NY (US)

(72) Inventors: Lishan Aklog, New York, NY (US); Brian deGuzman, Paradise Valley, AZ (US)

(73) Assignee: PAVmed Inc., New York, NY (US)

( * ) Notice: Subject to any disclaimer, the term of this patent is extended or adjusted under 35 U.S.C. 154(b) by 829 days.

(21) Appl. No.: 16/251,397

(22) Filed: Jan. 18, 2019

(65) Prior Publication Data

US 2019/0151619 A1    May 23, 2019

Related U.S. Application Data

(62) Division of application No. 14/956,141, filed on Dec. 1, 2015, now Pat. No. 10,252,034.

(60) Provisional application No. 62/085,838, filed on Dec. 1, 2014.

(51) Int. Cl.
*A61M 25/04* (2006.01)
*A61M 25/00* (2006.01)

(52) U.S. Cl.
CPC ........ *A61M 25/04* (2013.01); *A61M 25/0009* (2013.01); *A61M 25/0021* (2013.01)

(58) Field of Classification Search
CPC .............. A61M 25/04; A61M 25/0009; A61M 25/0021
See application file for complete search history.

(56) References Cited

U.S. PATENT DOCUMENTS

| 3,461,869 A | 8/1969 | Hargest |
| 3,719,737 A | 3/1973 | Vaillancourt et al. |
| 3,890,970 A | 6/1975 | Gullen |
| 4,534,761 A | 8/1985 | Raible |
| 4,676,782 A | 6/1987 | Yamamoto et al. |

(Continued)

FOREIGN PATENT DOCUMENTS

| CN | 201094764 Y | 8/2008 |
| CN | 201862119 U | 6/2011 |

(Continued)

OTHER PUBLICATIONS

Dictionary.com definition for the word point.

(Continued)

*Primary Examiner* — Laura A Bouchelle
*Assistant Examiner* — John A Doubrava
(74) *Attorney, Agent, or Firm* — Greenberg Traurig, LLP; Chinh H. Pham; Joshua I. Rudawitz

(57) ABSTRACT

Catheters for percutaneous applications are disclosed. The catheter according to example embodiments may comprise a substantially straight section, an anchoring section positioned proximal to the substantially straight section. The anchoring section can have a curvature for providing longitudinal traction with a tissue to anchor the catheter to the tissue and a pathway extending through the catheter for transporting fluids. The pathway may comprise a first section and a second section in fluid communication with each other, where the first section extends through the length of the straight section, and the second section extends through the anchoring section and has a curvature which mimics the curvature of the anchoring section.

10 Claims, 18 Drawing Sheets

(56) References Cited

U.S. PATENT DOCUMENTS

| | | |
|---|---|---|
| 4,781,694 A | 11/1988 | Branemark et al. |
| 5,797,870 A | 5/1998 | March |
| 5,964,744 A | 10/1999 | Balbierz et al. |
| 5,984,896 A | 11/1999 | Boyd |
| 6,391,018 B1 | 5/2002 | Tanaka et al. |
| 6,743,209 B2 | 6/2004 | Brown et al. |
| 8,075,630 B2 | 12/2011 | Ricci et al. |
| 8,932,263 B2 | 1/2015 | Rosenberg et al. |
| 8,940,002 B2 | 1/2015 | Goertzen |
| 10,252,034 B2 | 4/2019 | Aklog et al. |
| 2001/0053890 A1* | 12/2001 | Osborne .................. A61F 2/02 604/164.04 |
| 2002/0013615 A1 | 1/2002 | Haim et al. |
| 2002/0038111 A1 | 3/2002 | Alchas |
| 2003/0055402 A1 | 3/2003 | Zhou |
| 2003/0171723 A1 | 9/2003 | Ponzi |
| 2003/0216693 A1 | 11/2003 | Mickley |
| 2006/0111691 A1 | 5/2006 | Bolmsjo et al. |
| 2007/0093781 A1 | 4/2007 | Kugler et al. |
| 2008/0057106 A1* | 3/2008 | Erickson ............. A61K 9/0051 424/422 |
| 2008/0108950 A1 | 5/2008 | Rioux |
| 2009/0105659 A1 | 4/2009 | Bettuchi et al. |
| 2009/0163862 A1 | 6/2009 | Kaphusman |
| 2010/0106142 A1 | 4/2010 | Bolmsjo |
| 2011/0054448 A1 | 3/2011 | Bourne et al. |
| 2011/0152842 A1 | 6/2011 | Graffam et al. |
| 2011/0196410 A1 | 8/2011 | Besselink |
| 2012/0004616 A1 | 1/2012 | Mitra |
| 2012/0065630 A1 | 3/2012 | Berzak |
| 2012/0095440 A1 | 4/2012 | Islam |
| 2012/0116383 A1 | 5/2012 | Mauch et al. |
| 2012/0323174 A1 | 12/2012 | Shih |
| 2013/0218127 A1 | 8/2013 | Rosenberg et al. |
| 2015/0112309 A1 | 4/2015 | Rosenberg et al. |
| 2015/0196741 A1* | 7/2015 | Heilman ................ A61B 90/39 604/9 |
| 2015/0231368 A1 | 8/2015 | Hsueh et al. |
| 2016/0151608 A1 | 6/2016 | Aklog et al. |

FOREIGN PATENT DOCUMENTS

| | | |
|---|---|---|
| EP | 0348136 A2 | 12/1989 |
| EP | 1293162 | 3/2003 |
| JP | S58149765 A | 9/1983 |
| JP | 58-149765 | 9/1986 |
| JP | H10506026 A | 6/1998 |
| JP | 2002-191699 | 7/2002 |
| JP | 2002191699 A | 7/2002 |
| JP | 2003-529409 A | 10/2003 |
| JP | 2007-236628 A | 9/2007 |
| JP | 2009-268905 A | 11/2009 |
| JP | 2009-539426 A | 11/2009 |
| JP | 2010516436 A | 5/2010 |
| JP | 2011512183 A | 4/2011 |
| JP | 2011512885 A | 4/2011 |
| WO | 2000/29056 | 5/2000 |
| WO | 2007143305 A1 | 12/2007 |
| WO | 2008094952 A2 | 8/2008 |
| WO | 2009047490 A2 | 4/2009 |
| WO | 2009103758 A2 | 8/2009 |
| WO | 2010/022370 | 2/2010 |
| WO | 2011028632 A1 | 3/2011 |
| WO | 2014055547 A1 | 4/2014 |

OTHER PUBLICATIONS

Extended European Search Report for corresponding European application No. 15865776.7, dated Oct. 25, 2018 (14 pages).

PCT International Search Report and Written Opinion issued in International Application No. PCT/US2015/063221, dated Mar. 2, 2016.

* cited by examiner

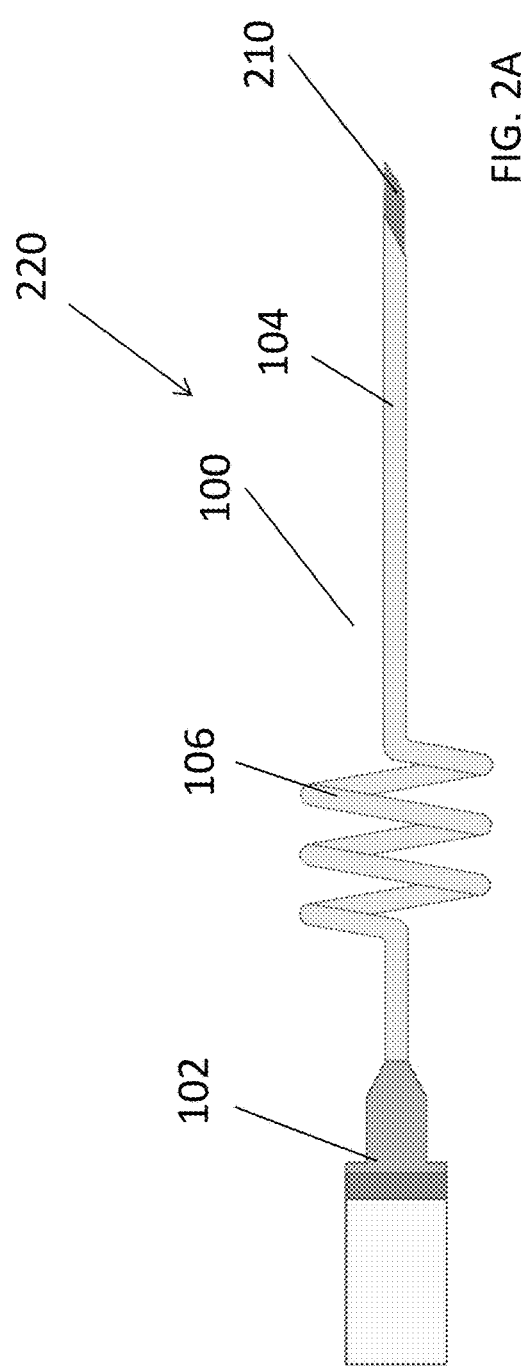
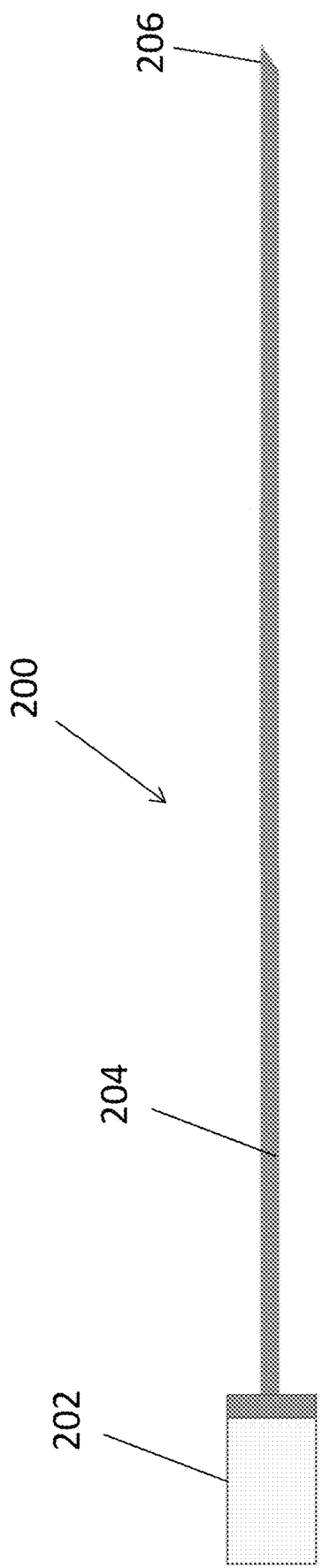

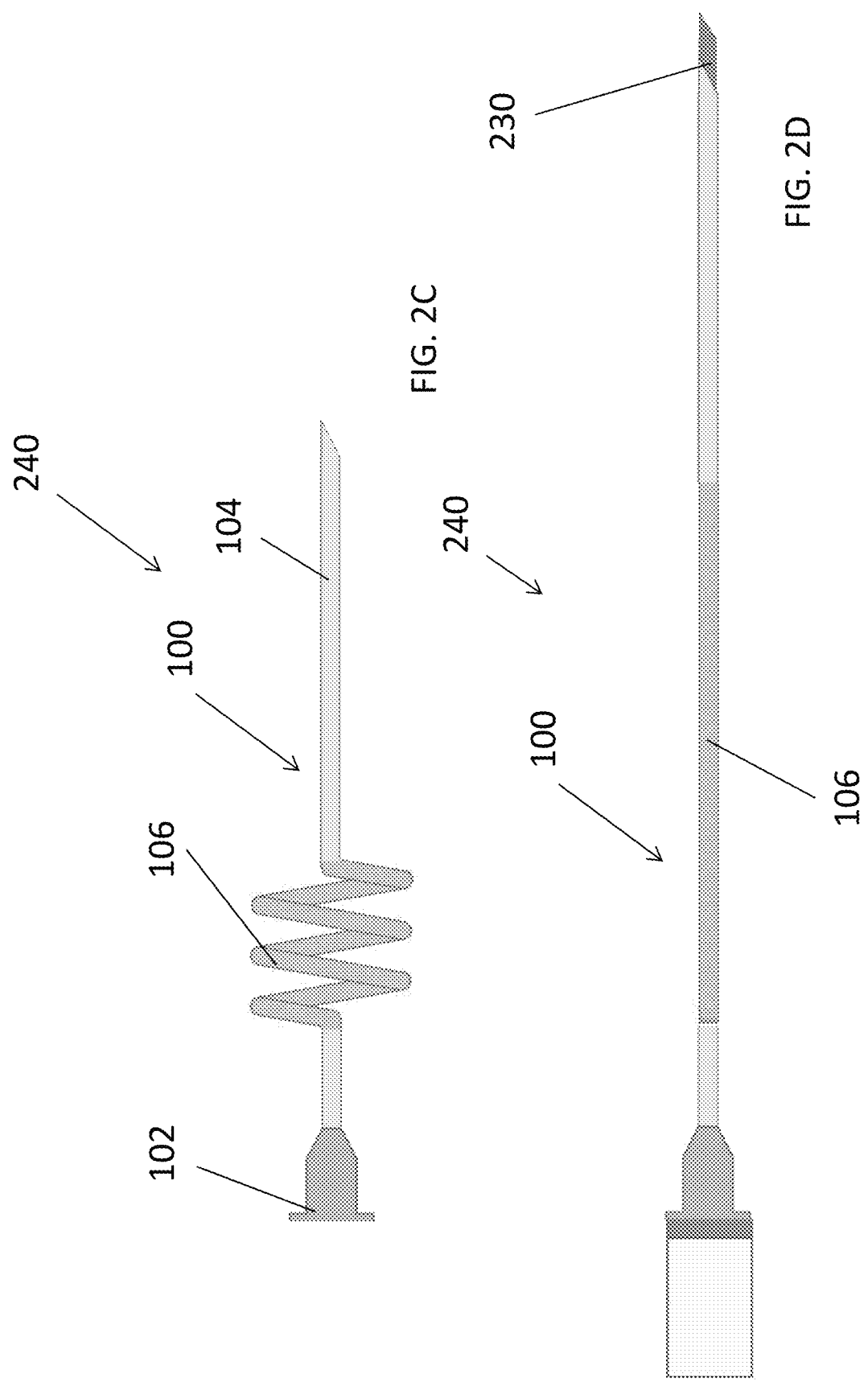

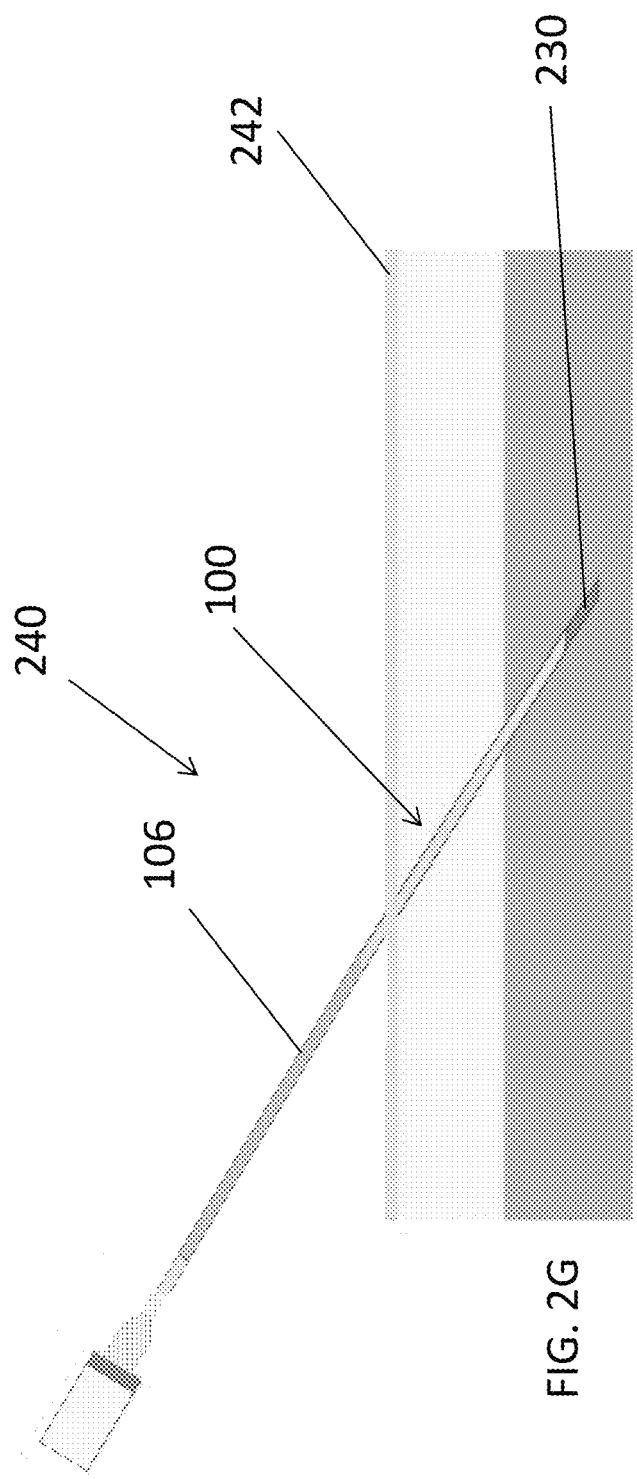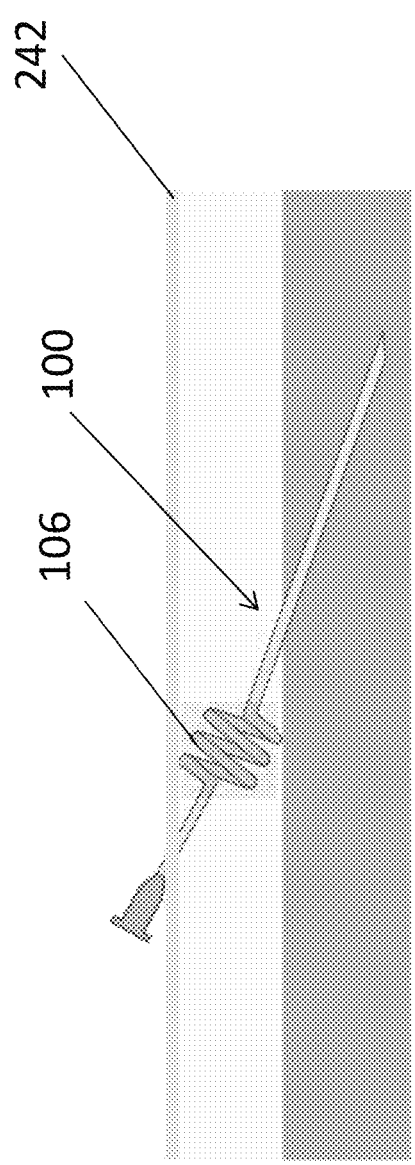

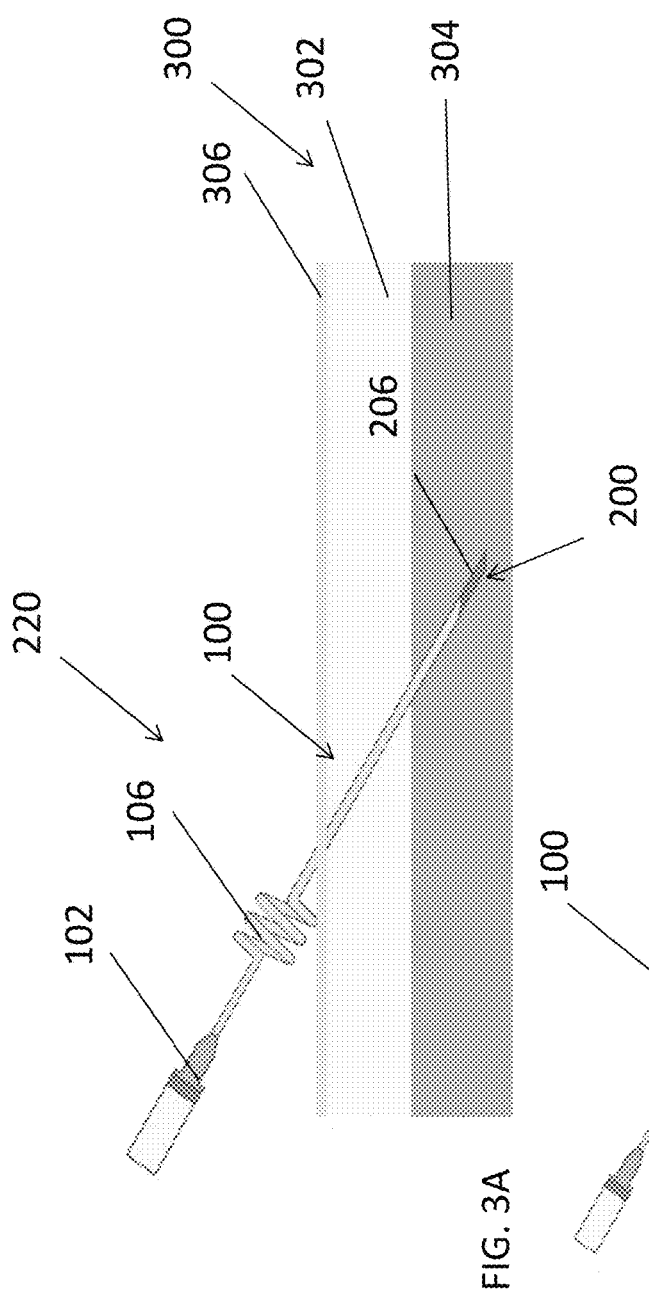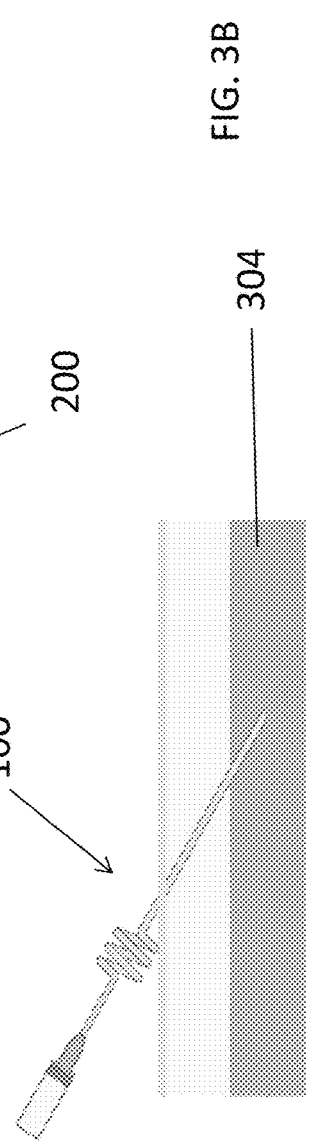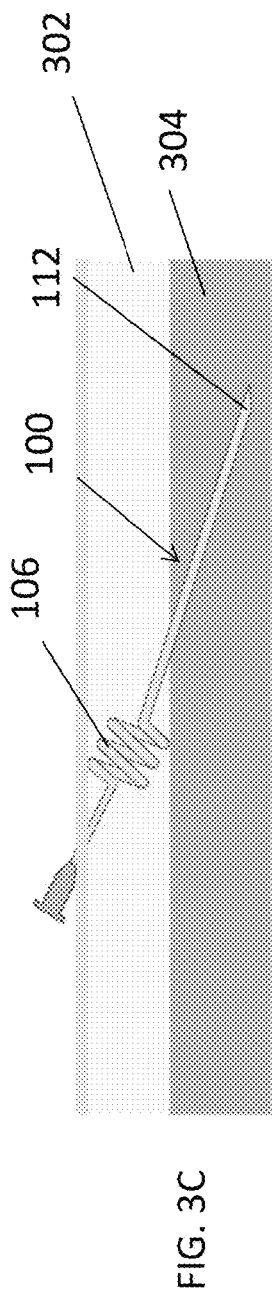

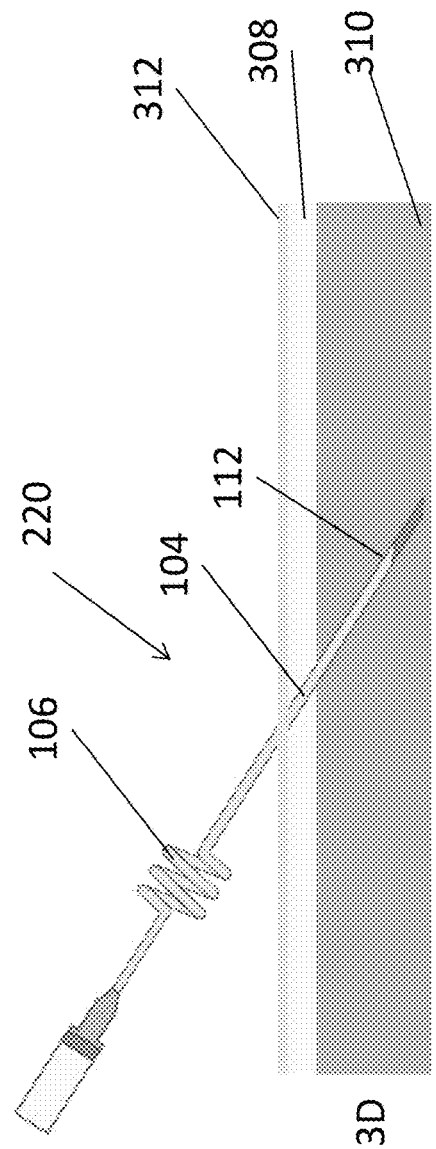
FIG. 3D
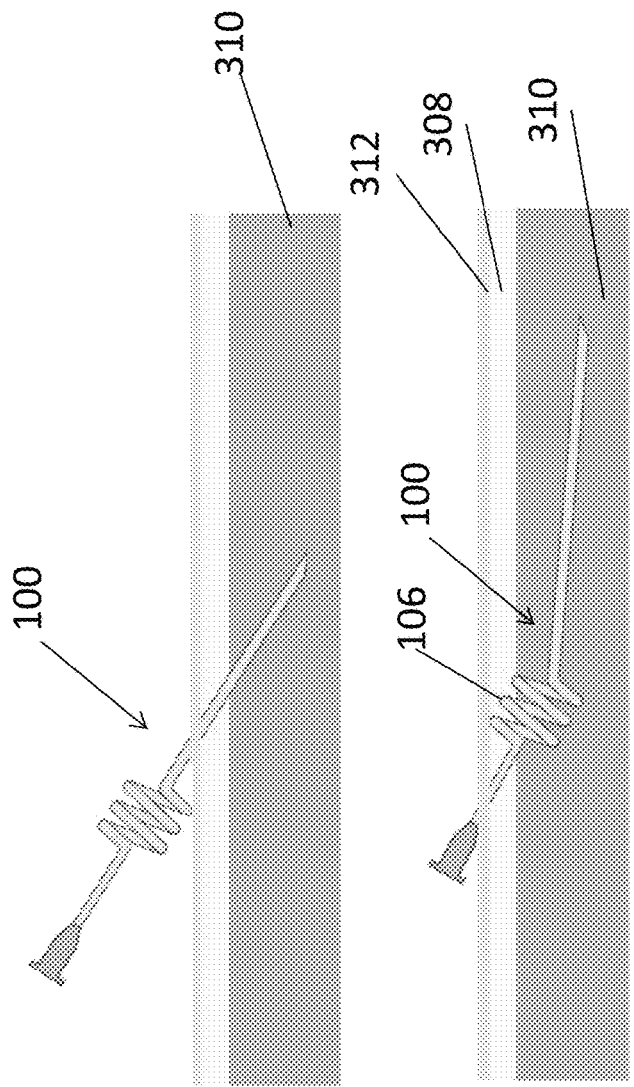
FIG. 3E
FIG. 3F

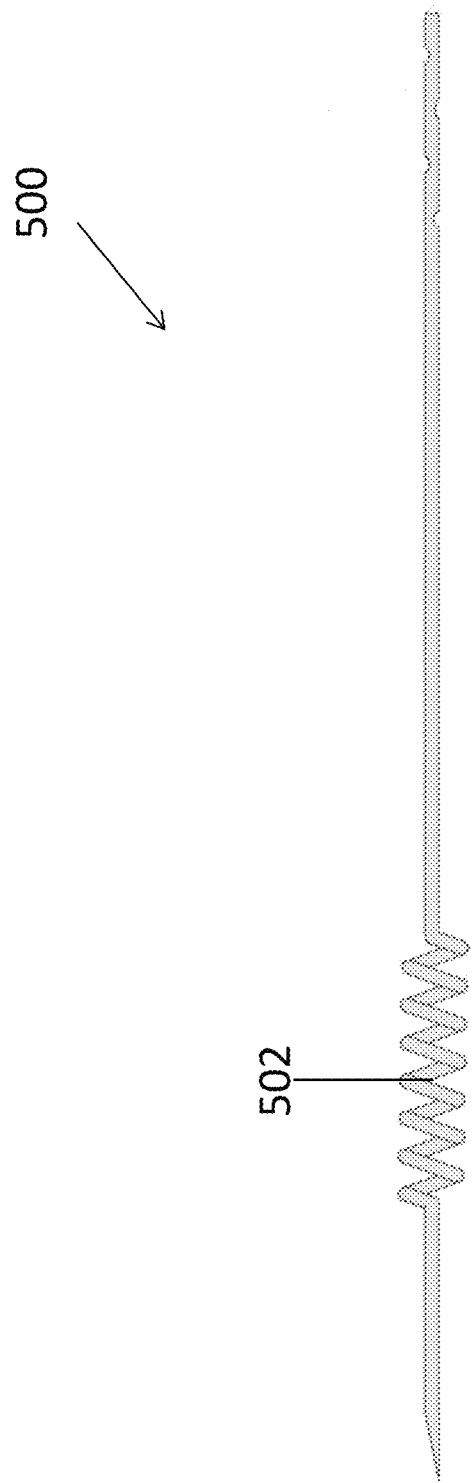

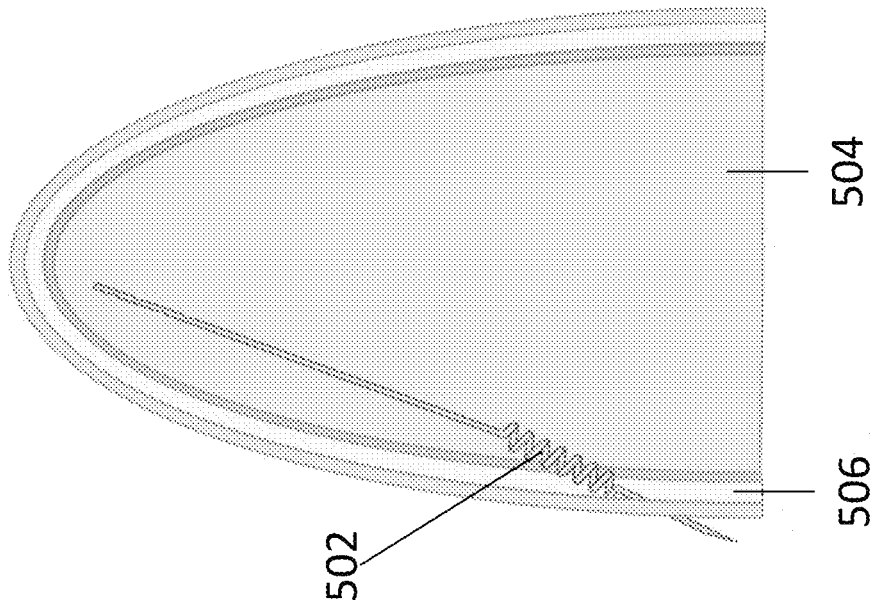

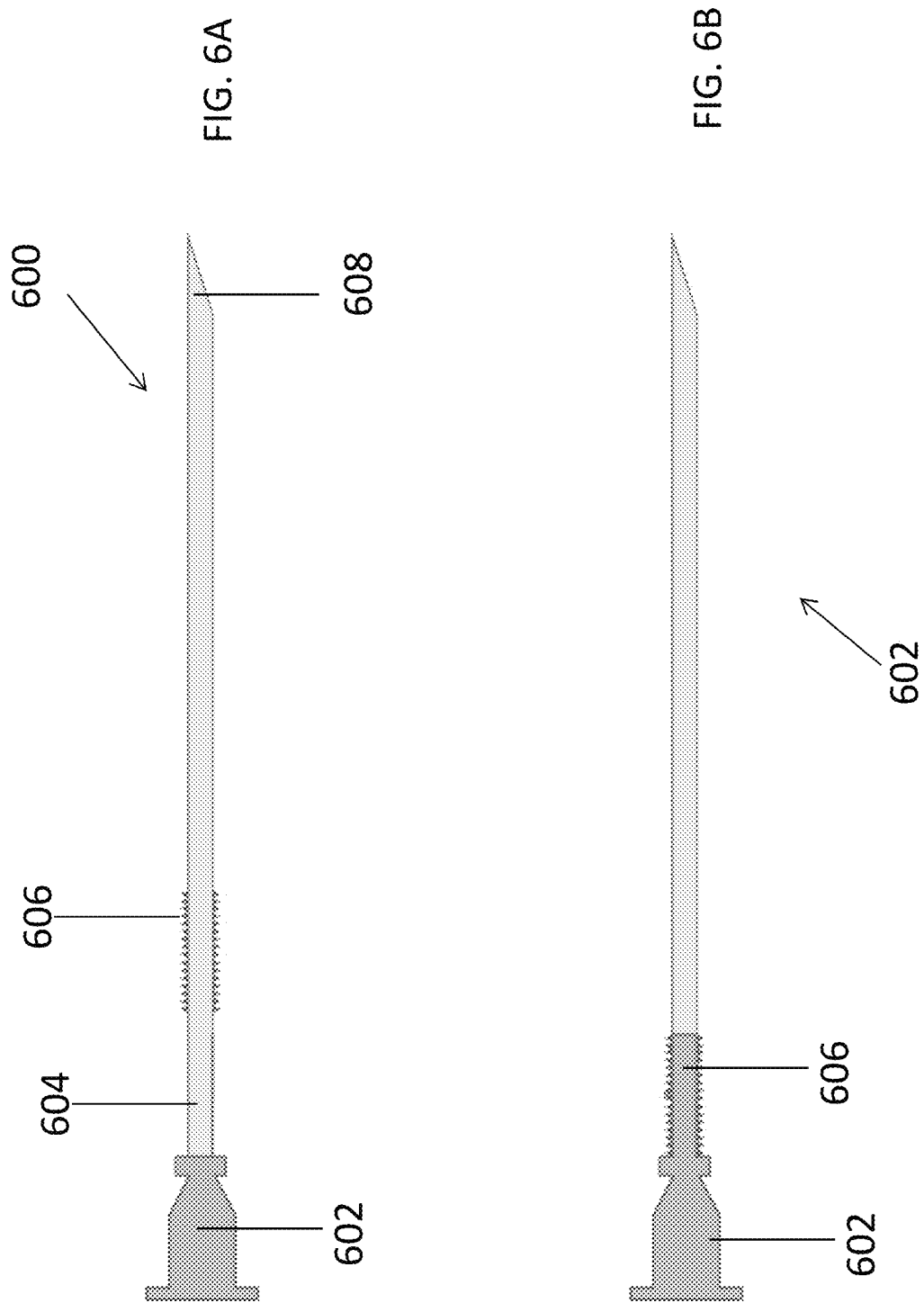

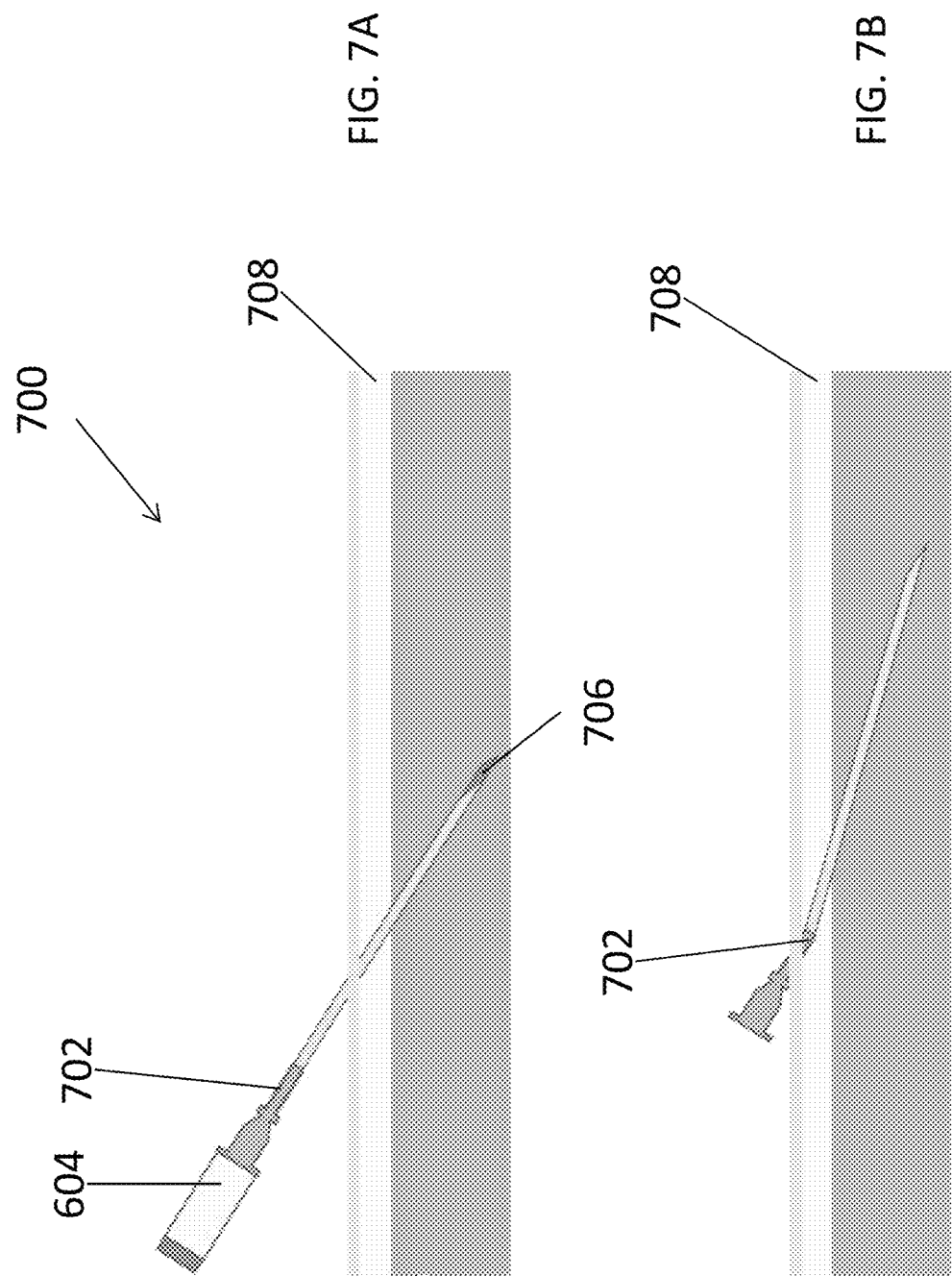

SELF-ANCHORING CATHETERS AND METHODS OF USE

CROSS-REFERENCE TO RELATED APPLICATION

This application is a divisional application of U.S. application Ser. No. 14/956,141 filed on Dec. 1, 2015, which claims the benefit of and priority to U.S. Provisional Patent Application No. 62/085,838, entitled "Self-Anchoring Catheters and Methods of Use", filed on Dec. 1, 2014, each of which is incorporated herein by reference in their entireties.

TECHNICAL FIELD

Example embodiments relate generally to catheters, more particularly, to percutaneous catheters. The present disclosure relates, in particular, to the use of a curved anchoring section for anchoring catheters within tissues without the need of additional devices or dressings.

BACKGROUND

A wide variety of catheters can be inserted into patients for short-term and long-term use. These catheters can be inserted into different types of anatomic structures including vascular structures (e.g. veins, arteries, cardiac chambers), body cavities and spaces (e.g. thoracic, pericardial, peritoneal, epidural, thecal) and visceral organs (e.g. stomach, intestines, bladder). They are used for various purposes including infusion of substances (e.g. fluids, medications, blood products, nutritional), withdrawal of blood or other bodily fluids for diagnostic or therapeutic purposes (e.g. drainage, decompression), monitoring of physiologic parameters (e.g. pressure, temperature) and as a conduit through which therapeutic or diagnostic instruments are passed.

Catheters commonly used for percutaneous applications include Percutaneous Venous Catheters (PVCs) and Central Venous Catheters (CVCs). PVCs are inserted through the skin into a peripheral vein, usually in the arm, and are the most common means of delivering fluids or medications into patients. CVCs are inserted through the skin into a central vein and usually remain in place for a long period of time, especially when the reason for their use is longstanding. PVCs and CVCs are secured into positions utilizing various means. For example, CVCs are sometimes inserted in more critical locations, and the catheters are sutured to the skin and frequently have eyelets, suture guides or other features to facilitate suturing. Other catheters are secured using simple or elaborate taping schemes. There are a wide variety of proprietary catheter anchoring devices being marked which uses a variety of adhesives, straps and other mechanisms.

Catheter dislodgment is an issue for a variety of reasons. Inadvertent dislodgement of certain catheters such as CVCs, chest tubes, large arterial sheaths and others can lead to serious complications including air embolism, pneumothorax, hemorrhage or even death. Furthermore, replacing dislodged catheters can expose patients to additional discomfort, interfere with the therapeutic regimen or other care and lead to complications from the reinsertion procedure. The economic burden resulting from dislodged catheters or the various efforts and protocols necessary to prevent dislodgement can be significant.

Accordingly, there is a need for catheters that can be anchored to the skin without a need for suturing, elaborate taping and/or additional anchoring devices.

SUMMARY

Devices, systems and methods for anchoring a catheter are disclosed herein. According to embodiments illustrated herein, there is provided a catheter capable of self-anchoring without the use of additional anchoring instruments. The catheter may include a substantially straight section, an anchoring section positioned proximal to the substantially straight section, where the anchoring section can have a curvature for providing longitudinal traction with the tissue to anchor the catheter to a tissue. The catheter may further include a pathway extending through the catheter for transporting fluids or through which instruments may be inserted into a patient, where the pathway can include a first section and a second section in fluid communication with each other. The first section can extend through the length of the straight section, and the second section extends through the anchoring section and having a curvature which mimics the curvature of the anchoring section.

In some embodiments, there is provided a catheter system including a straight section having a flexible portion capable of assuming a pre-determined curvature configured to provide traction with a tissue. The system may also include a shaping member with a curved section having the pre-determined curvature for shaping the flexible portion of the straight section into the pre-determined curvature, and a pathway extending through the length of the straight section for transporting fluids to and from the tissue, wherein when the shaping member is coupled to the flexible portion the flexible portion assumes the shape of the pre-determined curvature and the pathway may mimic the pre-determined curvature.

In some embodiments, there is provided a method for operating a self-anchoring catheter. The method may include inserting a catheter into a tissue, the catheter having a substantially straight section, an anchoring section positioned proximal to the substantially straight section and a pathway extending through the straight section, the anchoring section having a curvature for providing longitudinal traction with a tissue to anchor the catheter to the tissue and the pathway configured to mimic the curvature of the anchoring section. The method may also include advancing the catheter in a rotating fashion, until the anchoring section gains traction with the tissue, and anchoring the catheter using the traction created between the anchoring section and the tissue.

In some embodiments, there is provided a method for manufacturing a catheter. The method may include inserting a straight section of the catheter into a shaping member having a curved portion with a pre-determined curvature, the straight section having a flexible portion capable of being molded into the pre-determined curvature. The method may also include shaping the flexible portion of the straight section to assume the pre-determined curvature, and removing the straight section from the shaping member, wherein the flexible portion of the straight section retains the pre-determined curvature.

BRIEF DESCRIPTION OF THE DRAWINGS

Illustrative, non-limiting example embodiments will be more clearly understood from the following detailed description taken in conjunction with the accompanying drawings.

FIG. 2A and FIG. 2B illustrate a catheter system having a helical shaped self-anchoring section and an insertion needle for assisting the insertion of the catheter system;

FIG. 2C and FIG. 2D illustrate a catheter with a flexible anchoring portion and a rigid insertion needle capable of straighten the flexible anchoring portion;

FIG. 2G and FIG. 2H illustrate a catheter system with a flexible anchoring section inserted into a vessel layer;

FIGS. 3A-3F illustrate a catheter system having a helical shaped self-anchoring section being inserted into anatomic structures;

FIG. 5A illustrates a thoracic catheter having a helical shaped self-anchoring section;

FIG. 5B illustrates a thoracic catheter having a helical shaped self-anchoring section being inserted into an anatomic structure;

FIG. 6A and FIG. 6B illustrate catheters having threaded self-anchoring sections;

FIG. 7A and FIG. 7B illustrate a catheter having a threaded self-anchoring section being inserted into an anatomic structure;

DETAILED DESCRIPTION OF THE EMBODIMENTS

Figure 1A:
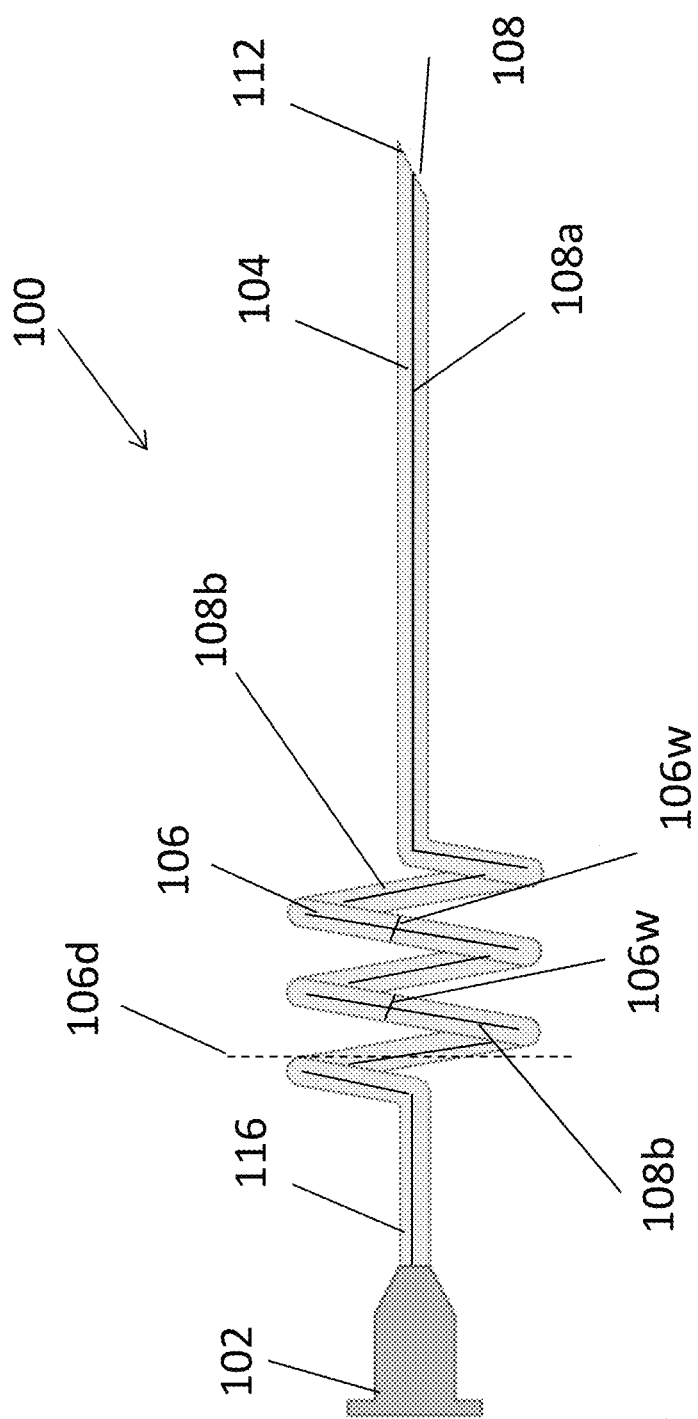
FIG. 1A illustrates a catheter with a helical shaped self-anchoring section.
Figure 1B:
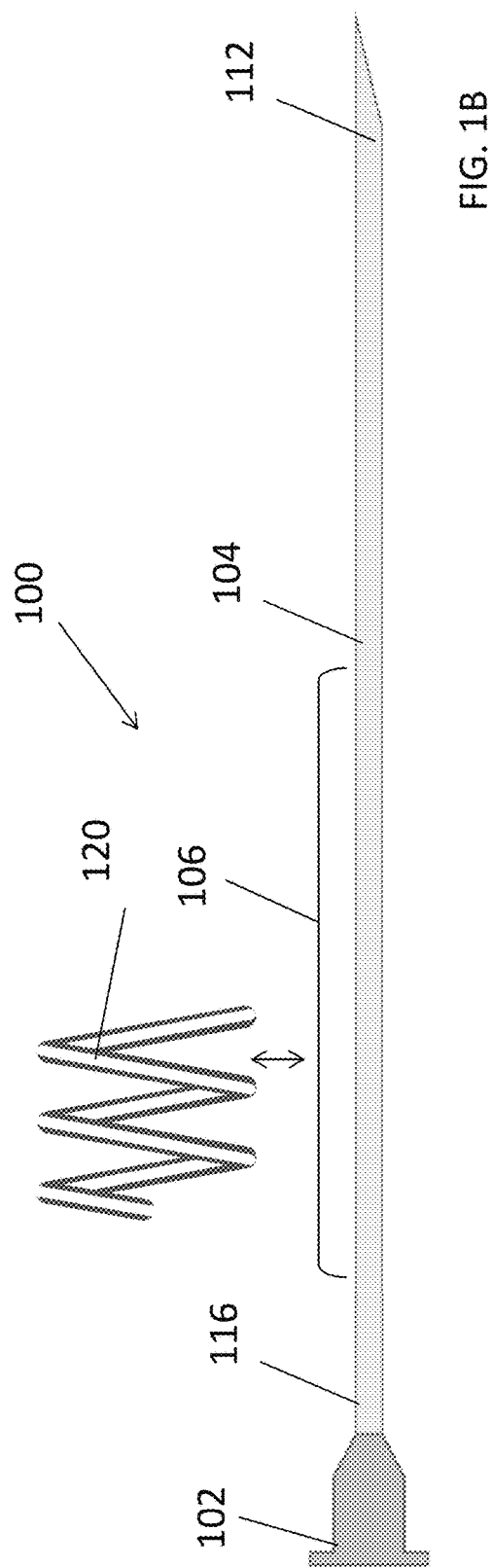
FIG. 1B and FIG. 1C illustrate a catheter with a rigid insert for shaping a portion of the catheter.
Figure 1C:
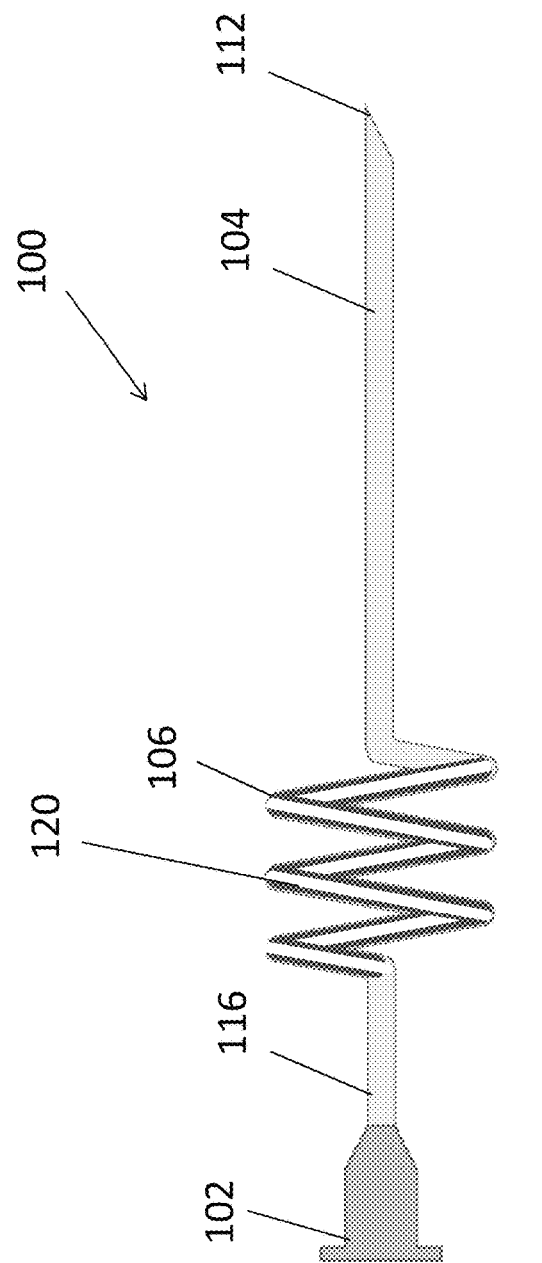
Figure 1D:
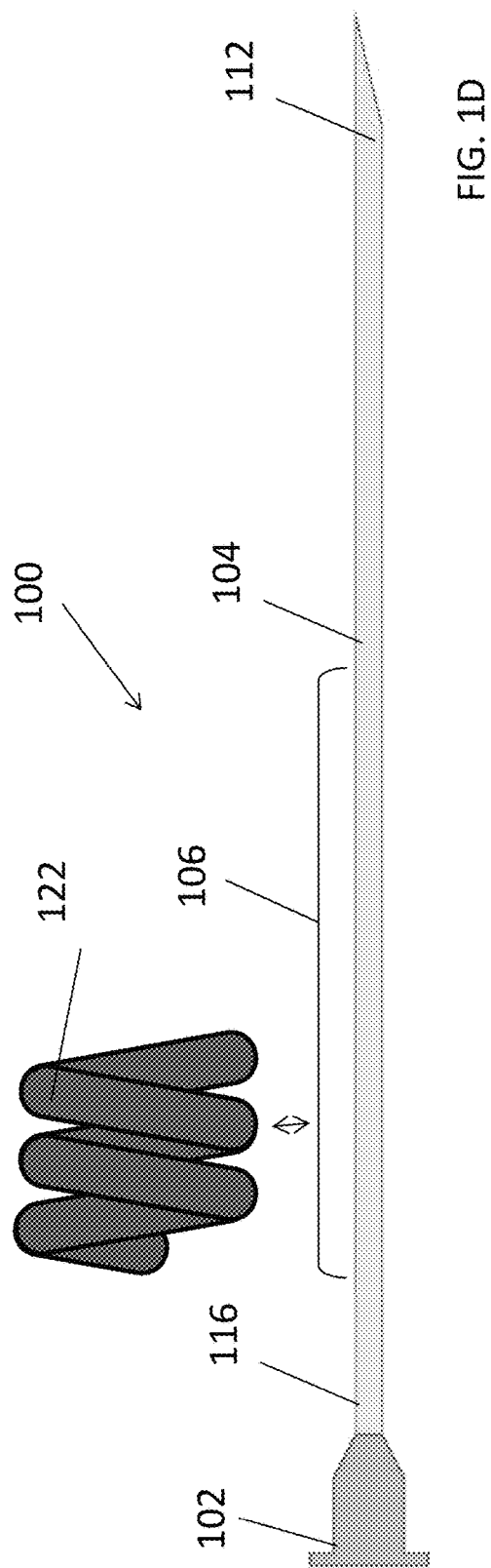
FIG. 1D and FIG. 1E illustrate a catheter with a jacket for shaping a portion of the catheter.
Figure 1E:
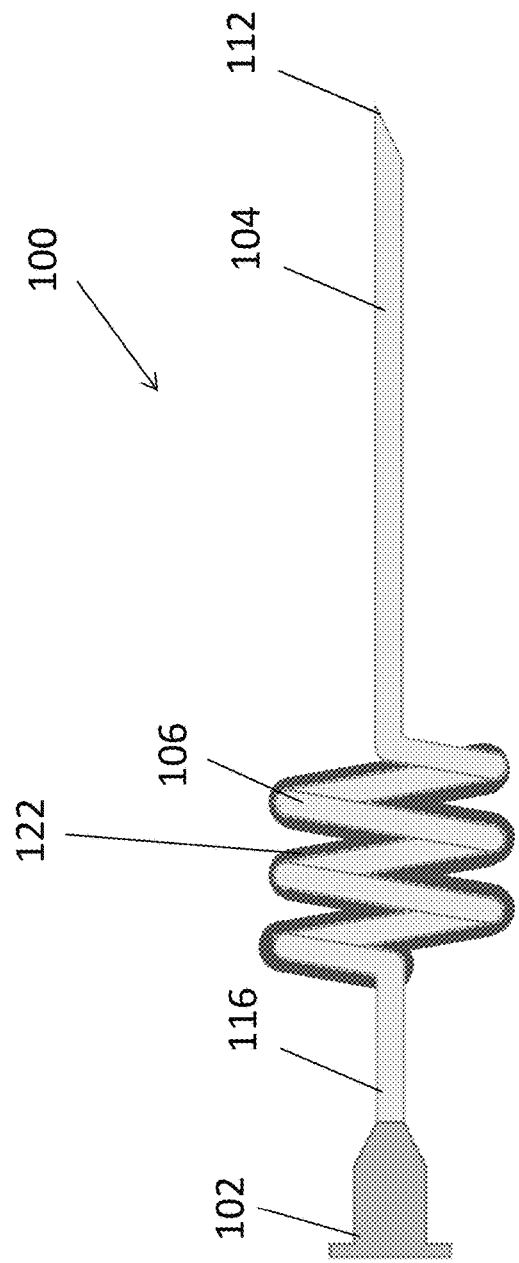

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the present disclosure generally provide self-anchoring catheters and catheter systems for percutaneous applications. The various embodiments of the present disclosure can be used for infuse or withdraw fluids from bodily tissues, and to provide short or long term venous accesses.

FIG. 1 illustrates a catheter 100 in accordance with various embodiments of the present disclosure. Referring to FIG. 1, the catheter 100 can include a hub 102 section and a pathway 108 extending through the length of the catheter 100. The hub 102, as illustrated, may be positioned at a proximal end of the catheter 100 and designed to be connected to a wide variety of instruments, such as but not limited to, an infusion source, a withdrawal mechanism, a monitoring device or serve as a portal of entry for diagnostic or therapeutic instruments. To that end, the hub 102 may be of any shape or dimension so long as it can be attached to the desired instrument.

The catheter 100 may also include a catheter or body section 104 configured for communicating with anatomic structures. The catheter section 104 can be directly connected to the hub 102 where a first section 108a of the pathway 108 may extend through the entire length of the catheter section 104. The overall length of the catheter section 104 can vary to better accommodate the insertion of the catheter 100 into different types of anatomic structures. In some embodiments, the catheter section 104 may further include a tip located at a distal end 112, where the catheter section 104 and the distal tip 112 can be placed at desired locations for transporting (i.e., delivering or withdrawing) fluids. In some embodiments, the catheter section 104 may be substantially straight in nature for overcoming multiple layers of tissues of an anatomic structure. The catheter section 104 can then place the distal tip 112 at the desired locations, where fluids can be delivered or withdrawn at the distal tip 112 and then through the pathway 108. To better assist the insertion and anchoring of the catheter at the various types of anatomic structures, the catheter section 104 may be constructed to be rigid, semi-rigid or flexible and may possess one or more lumens designed for different types of venous applications. In general, the catheter 100 and its various components may be made from any material that is biocompatible, including, but not limited to, plastic, metal or ceramic.

In some embodiments, as shown in FIG. 1, for anchoring the catheter 100 at a surgical site, the catheter 100 can include an anchoring section 106 designed to secure the catheter 100 onto a tissue without using sutures, tapes or additional anchoring apparatuses. The anchoring section 106 may be designed to be directly connected the hub section 102, or in some embodiments, a proximal catheter section 116 may be placed between the anchoring section 106 and the hub section 102, where the proximal catheter section 116 may be substantially straight in nature and the length of the section 116 can vary to better accommodate the anchoring and insertion of the catheter into different anatomic structures. Fluids can be transported through the entire length of the catheter 100, from the hub 102 to the distal tip 112, via the pathway 108 which extends through the entire anchoring section 106.

Referring to FIG. 1, to anchor the catheter 100 at a tissue site, the anchoring section 106, in some embodiments, can be curved to assume a corkscrew like helical configuration, designed to anchor into tissue structures. This helical structure can include a plurality of turns spaced apart at certain pitch designed to create a traction force with surrounding tissue. Each turns of the helical structure can in general have a width 106w that is substantially similar to the diameter 104w of the catheter section 104 or the rest of the catheter 100 for that matter. Dimensions and pitch distances of the anchoring section 106 can be configured to optimize the traction between the helical turns and the tissue body. For example, the diameter or width 106d of the helical portion can be substantially larger than the opening created by the catheter section 104 when the catheter is initially inserted into the tissue, thereby ensuring the turns of the helical anchoring section 106 can be securely pushed against the surrounding tissues. It should be appreciated that the length provided to the anchoring section 106, in some embodiments, should be sufficient to optimize traction, and that although a helical design is provided, other geometric designs can be implemented, so long as such a design permits that anchoring section to be advanced to secure the device in place. In some embodiments, for a 1 mm diameter PVC, the anchoring section 106 can have about two to six turns, the helix diameter can be about two to six times the catheter diameter (e.g., about two to six mm), and the pitch between the turns can be about two to four mm. During an anchoring process, as the catheter 100 is inserted into a tissue, the catheter 100 may be rotated clockwise or counter-clockwise until the anchoring section 106 can be placed substantially underneath at least one layer of tissue (i.e., a layer of skin), such that the plurality of helical turns can generate a traction force sufficient with the tissue to resist a longitudinal displacement of the catheter 100. Leaving at least one helical turn proximal to the anchoring tissue allow the catheter 100 to not only resist dislodgement from a traction force but also prevents the catheter 100 from advancing further into the patient from a pushing force. It should be appreciated that the anchoring section 106 can be of any shape or dimension so long as it can create sufficient traction forces with the surrounding tissues to resist against dislodgement. In some embodiments, once the catheter 100 is secured in place, fluids can be transported through the pathway 108, where a second portion 108b of the pathway 108 may be designed to mimic the curvatures of the helical portion, such that fluids flows through each turns within the helical portion. The second section 108b of the pathway 108 can be entirely housed within the turns of the helical portion and in direct communication with the first section 108a of the pathway 108. The anchoring section 106 as shown in FIG. 1 effectively allows tissues to be lodged between each turns of the helical portion, thereby optimizing the traction force between the catheter 100 with the surrounding tissues. Furthermore, the length and diameter of the helical portion, as well as the number of turns and the pitch distance between turns, can be optimized to better anchoring the catheter in different anatomic structures. It should be appreciated that although only one anchoring section is provided, to the extent that certain applications are contemplated, the device can be provided with multiple anchoring sections. The availability of multiple anchoring sections can assist in securing the device across an area with different tissues. For example, a catheter may include two or more anchoring sections for anchoring the catheter in two different anatomic layers (e.g., skin and fascia). The helical corkscrew like configuration of the anchoring section 106 can be formed in a variety of ways. In order to serve its anchoring role, the anchoring section 106 may be configured to resist straightening during application of a traction force. As such, the anchoring section 106 may be designed to possess some rigidity. In some embodiments the entire catheter 100 may be substantially rigid, in which case the helical anchoring portion 106 can be created as part of a single piece by shape molding that segment using common techniques (e.g. bending around a mandrel, heat shaping or fabricating it in that shape from the onset). In some embodiments where the distal straight portion of the catheter 104 is substantially flexible, the device can be constructed from a single piece by treating the helical portion in such a way to render it more rigid or by altering the material as it is being created (e.g. during an extrusion). In some embodiments, the catheter 104 can be created from multiple parts which render the distal straight portion substantially flexible and the proximal helical portion more rigid. For example, a relatively rigid insert 120, as illustrated in FIG. 1B and FIG. 1C, may be applied to the anchoring section 106 (which may be flexible) to create a helical shaped portion. Or as illustrated in FIGS. 1D and 1E, a jacket 122 with a helical shape can be applied to the anchoring portion 106 of the catheter to render the anchoring portion 106 more rigid and also shape the anchoring section 106 into a helical configuration.

For the purpose of better assisting the initial insertion into a tissue, the catheter 100 can be equipped with a distal tip 112 that may be sharp and pointed and designed to penetrate tissues. Or, in some embodiments, an integrated needle or an insertion kit can be used to firstly penetrate the tissue and then guide the catheter 100 to the desired anatomic location. FIGS. 2A and 2B are diagrams illustrating an insertion needle 200 designed to be integrated with the catheter 100 for an initial penetration into a tissue. Referring to FIG. 2A, the insertion needle 200 can include a proximal needle hub 202 that is connectable to the hub section 102 of the catheter 100. The proximal needle hub 202 can be connected to a substantially straight needle section 204, where the needle section 204 may be of a diameter that is less than the diameter of the pathway 108, such that the needle section 204 can be inserted through the pathway 108. The needle section 204 can further include a distal tip 206 that may be sharp and pointed and designed to pierce through tissues. Now referring to FIG. 2B, in some embodiments, a catheter system 220 can have the catheter 100 integrated with the insertion needle 200 for percutaneous applications. In use, the entire needle section 204 can be fed through the catheter 100 at the catheter's hub section 102, as illustrated in FIG. 2B, where the length of the insertion needle's 200 needle section 204 can be optimized such that when inserted through the catheter 100, the distal tip 206 of the needle section 204 protrudes out of the catheter 100 just slightly. To accomplish this integration with the catheter 100 while still be able to pierce through tissues (i.e., skins and vessels), the integration needle 200 can consists of shape memory metal such as nitinol or spring metal, which possesses the necessary flexibility to travel through the helical configuration, yet also stiff enough to penetrate various anatomic structures.

During a catheter anchoring process, the catheter 100 can be firstly inserted through a layer of skin and into an appropriate anatomic structure with the integrated needle 200 until the anchoring section 106 (i.e., helical portion) reaches the skin entry point. The catheter 100 can then be rotated until all or most of the anchoring section 106 became submerged underneath the skin. Subsequently, the catheter 100 can be covered with a simple dressing, where the dressing and additional treatment of the entry point can be performed to prevent inadvertent rotation of the catheter 100. In this manner, for at least the reason that the diameter of the helical portion is substantially larger than the entry opening in the skin, the anchoring section 106 can resist dislodgement in longitudinal direction. In some embodiments, removing the catheter 100 can include removing the dressing, rotating the catheter 100 in the opposite direction of the insertion rotation until the helical portion is completely outside the tissue body and then slide the remaining distal straight catheter section 104 out of the patient.

Figure 2E:
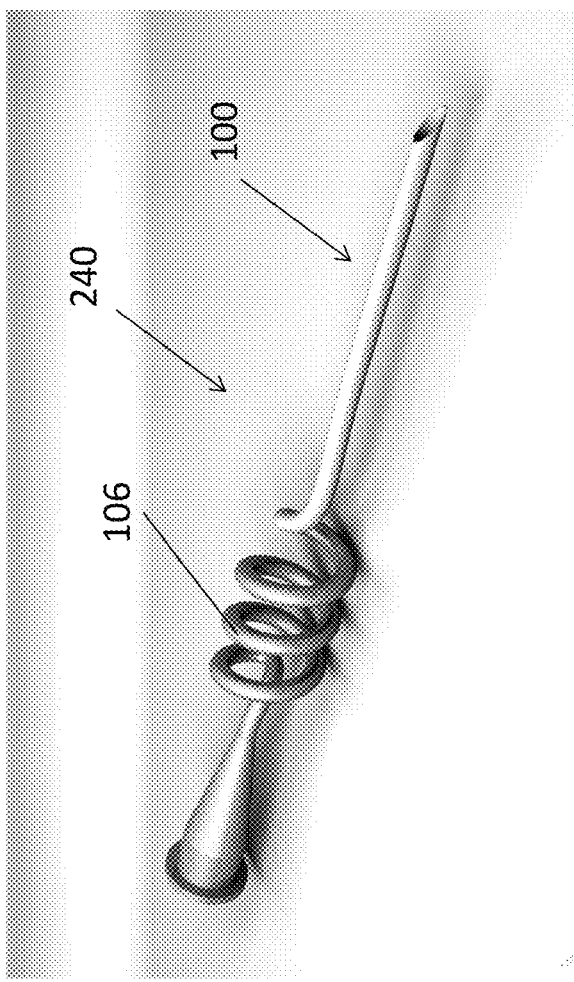
FIG. 2E and FIG. 2F illustrate a catheter system with a flexible anchoring section and a rigid insertion needle.
Figure 2F:
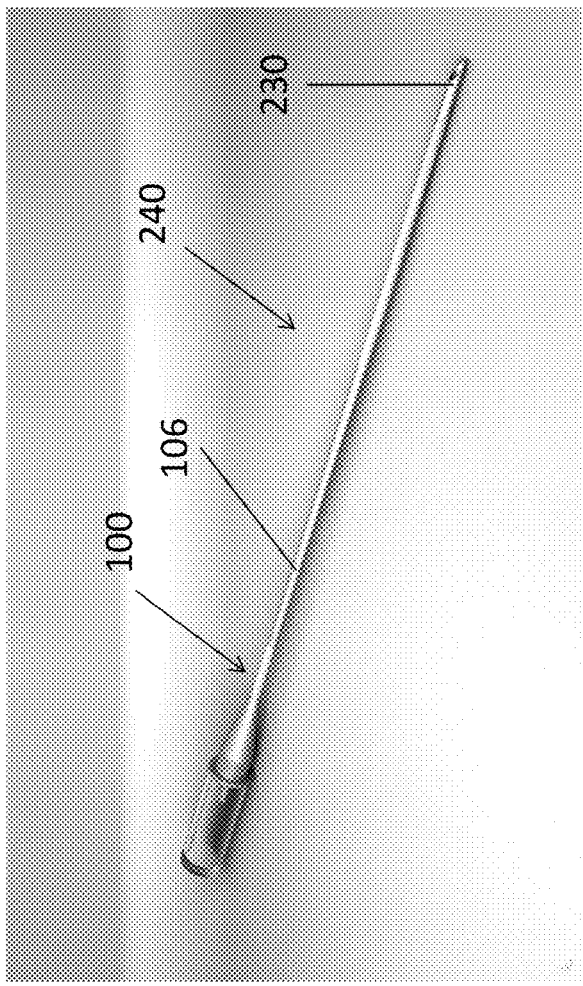

In some embodiments, as shown in FIG. 2C and FIG. 2D, the helical anchoring portion 106 of the catheter 100 may be fabricated so that it is stiff enough to resist straightening under traction forces but flexible enough and possesses shape memory so that it may be straighten when a rigid insertion needle 230 is advanced through the catheter's 100 lumen. In this embodiment, the catheter 100 and insertion needle 230 assemble 240 may be provided to an operator just as a traditional device would. The portion of the catheter with helical shape memory (e.g., anchoring portion 106) can be indicated by a different color or other markings so that the operator can know where the helical portion begins during the insertion process. As illustrated in FIG. 2D, when a rigid insertion needle 230 is inserted through the anchoring section 106, the anchoring section 106 may be flexible enough to assume a substantially straight shape. FIG. 2E and FIG. 2F illustrate an exemplary embodiment of the catheter system presented in FIG. 2C and FIG. 2D. As illustrated in FIG. 2E, the anchoring section 106 may be sufficiently flexible to assume other geometrical configurations, and the anchoring section 106 may be marked in a distinct color so an operator may know where the section 106 begins and ends. In some embodiments, as illustrated in FIG. 2F, a rigid insertion needle 230 may be applied to the catheter 100 to straight out the anchoring section 106.

During a catheter anchoring process, as shown in FIG. 2G and FIG. 2H, the straight catheter/needle assemble 240 may be inserted through a layer of skin 242 and into an appropriate anatomic structure until the marked, but current straightened, helical portion 106 is near the skin entry point. When the needle 230 is removed and no longer straightening the helical portion 106, this portion 106 takes its helical configuration based on shape memory. The helical portion 106 can then inserted through the skin 242 using the same rotational motion.

In some embodiments, the catheter system 220 as shown in FIG. 2B can be conveniently deployed in anatomic structures where blood vessels lay closely or far away from the skin layer. Firstly, a blood vessel can be identified through direct visualization, palpation or using some imaging modality. Subsequently, catheters such as peripheral vascular catheters (PVCs) integrated with anchoring sections that are similar to the anchoring section 106 described in FIG. 1 can be used for percutaneous applications. FIGS. 3A-3C illustrate the catheter 100 being anchored in an anatomic structure 300 where the thickness of the subcutaneous tissue layer 302 is sufficiently large to anchor a substantial portion of the anchoring section 106 within. For such anatomic structures, during a catheter anchoring process, to reach a vessel layer 304, the catheter system 220, where the insertion needle 200 is integrated within the catheter 100, may need to firstly pierce through a layer of skin 306 and a layer of subcutaneous tissue 302 using the sharp distal needle tip 206. Referring to FIG. 3A, the catheter system 220 can then be rotated to induce the anchoring section 106 through the initial entry site and into the subcutaneous tissue 302. Once at least a substantial portion of the anchoring section 106 can be positioned within the subcutaneous tissue layer 302, the insertion needle 200 can be withdrew from the catheter system 220 by pulling the needle 200 out of the catheter 100 at the hub section 102. Illustrated in FIG. 3B is the catheter 100 inserted into the vessel layer 304 after the insertion needle 200 has been removed from the catheter system 220. Referring now to FIG. 3C, the catheter 100 can be securely anchored at the subcutaneous tissue layer 302 where the distal tip 112 is in contact with the vessel layer to infuse or withdraw fluids.

Similarly, as illustrated in FIGS. 3D-3F, the catheter system 220 can be readily deployed in an anatomic structure where the thickness of the subcutaneous tissue layer 308 may be insufficient to anchor the anchoring section 106. Referring now to FIG. 3D, after the distal end 112 and a portion of the catheter section 104 has penetrated through the subcutaneous tissue 308 layer to reach the vessel layer 310, the catheter system 220 may be rotated to induce a horizontal motion to the catheter section 104 until a substantial portion of the anchoring section 106 can be position within the vessel layer 310. The helical portion of the anchoring section 106 can create a traction force with the vessel layer 310, effectively securing the catheter 100 with in the vessel layer 310. FIG. 3E illustrate the catheter 100 being inserted into the vessel layer 310 with the insertion needle removed. Referring now to FIG. 3F, after the catheter 100 is securely anchored in place, the anchoring section 106 may be entirely or partially anchored into the vessel layer 310 depending on the topography of that particular anatomic structure.

Figure 4A:
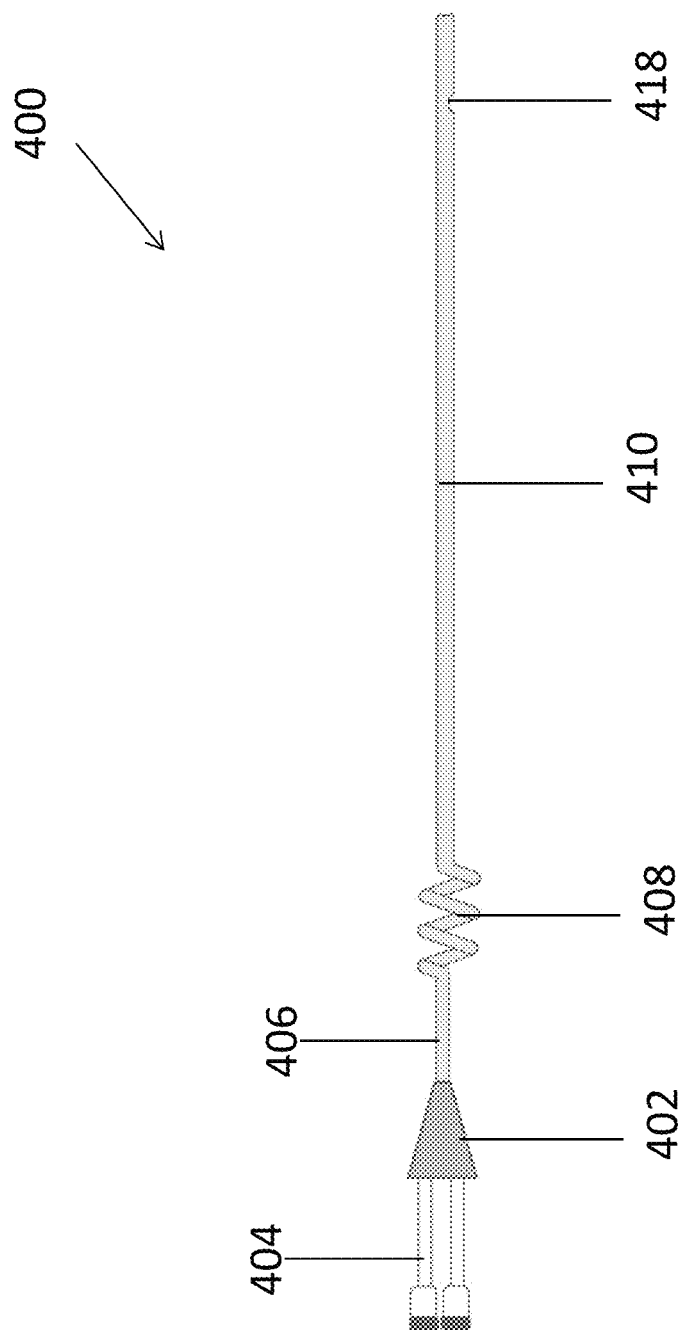
FIG. 4A illustrates a central vascular catheter having a helical shaped self-anchoring section.
Figure 4B:
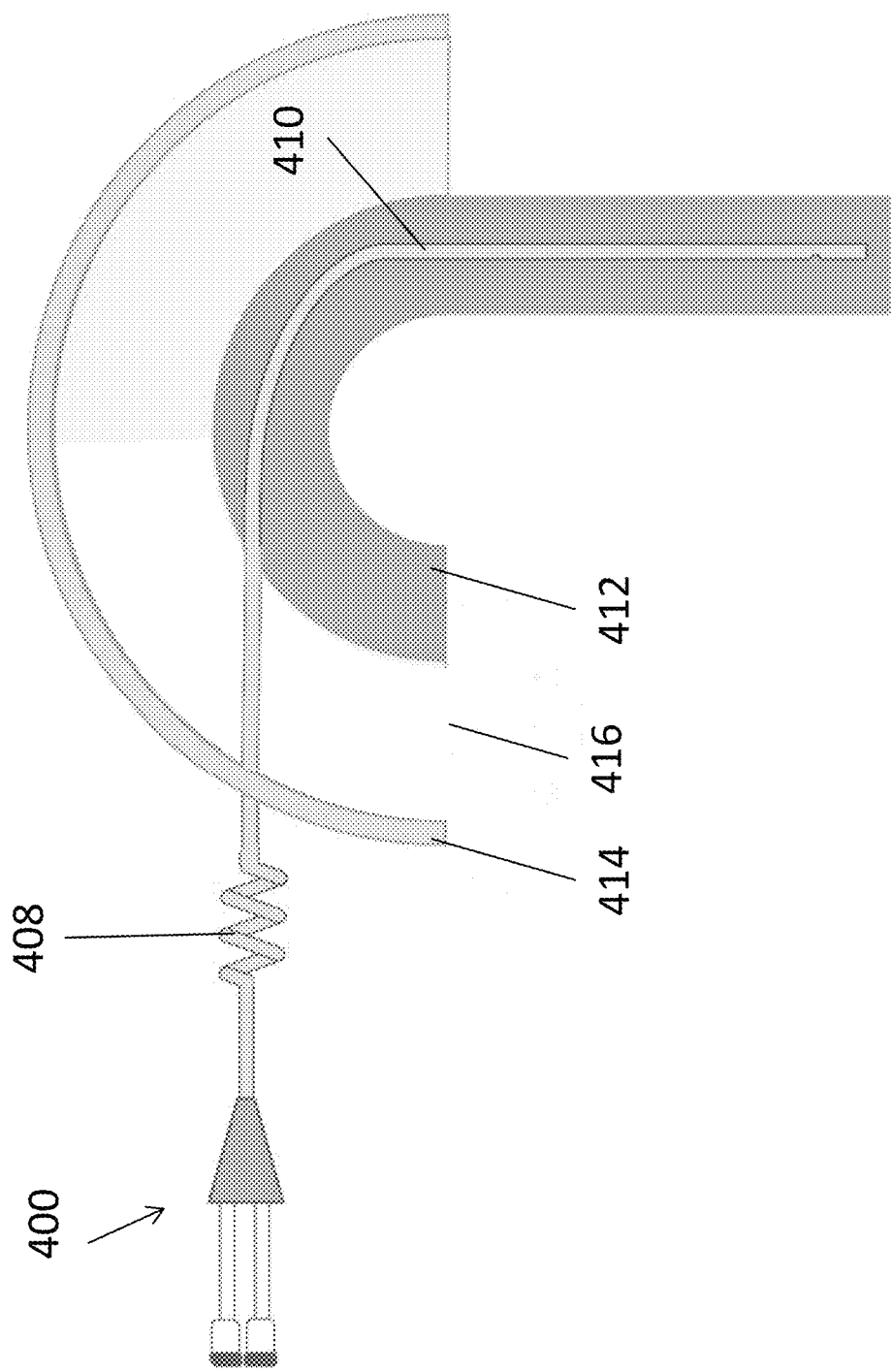
FIGS. 4B and 4C illustrate a central vascular catheter having a helical shaped self-anchoring section being inserted into an anatomic structure.
Figure 4C:
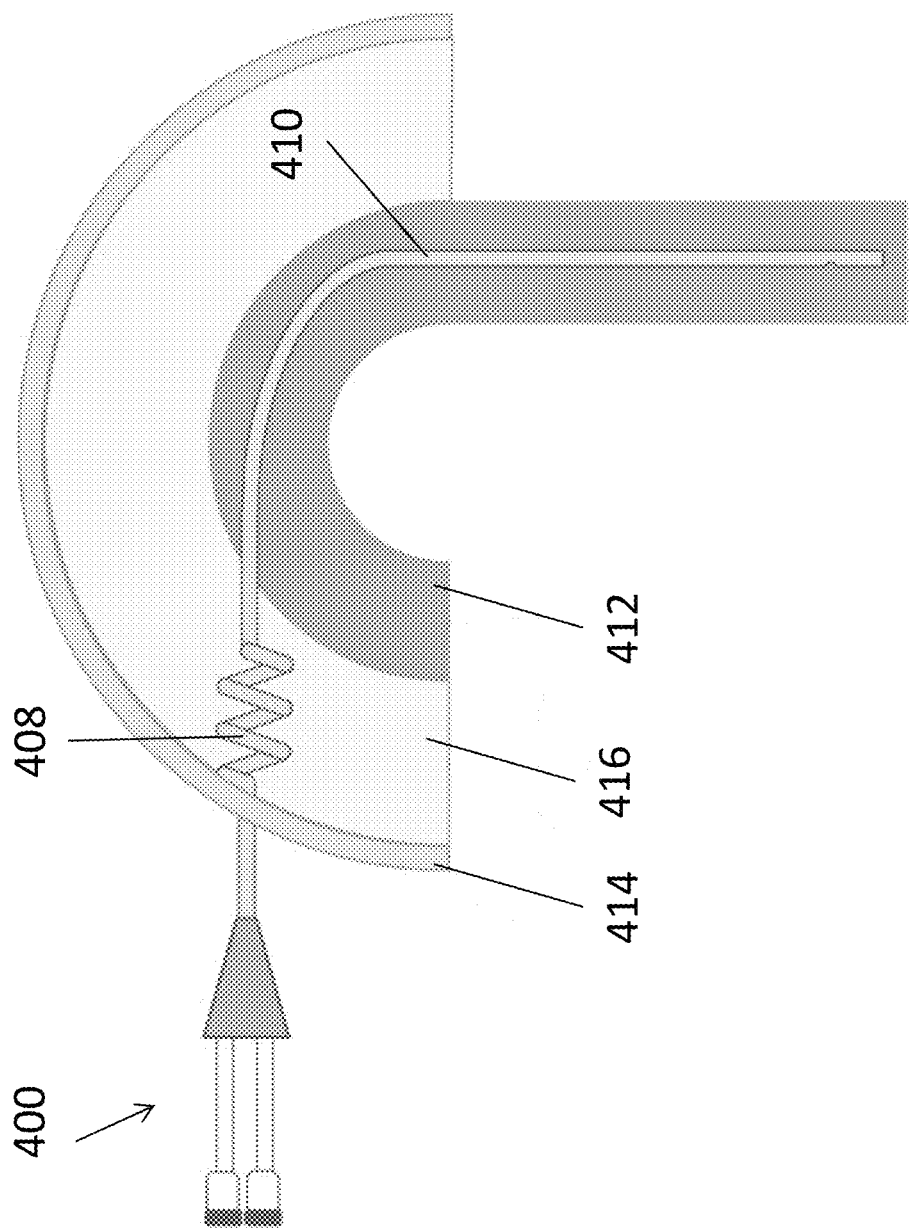

It should also be appreciated that the helical configuration can also be used on central vascular catheters as illustrated in FIG. 4A. Similar a traditional central vascular catheter, catheter 400 as illustrated in FIG. 4A can possess a proximal hub section 402 with one or more ports 404 and a catheter portion with one or more lumens 418. The catheter portion can include a substantially straight proximal section 406, a helical anchoring section 408 and a distal section 410. Similar to the peripheral vascular catheter 200, the helical anchoring section 408 can also be rigid or semi-rigid, and an insertion of the central vascular catheter 400 can be facilitated with an insertion needle or an insertion kit. In some embodiments, the central vascular catheter 400 can be inserted into an anatomic structure to reach a blood vessel as illustrated in FIGS. 4B and 4C. An insertion kit can be used to assist the access to vessel 412, where a finder needle and a guide wire can be used to advance the straight proximal section 406 off the catheter 400 into position. Subsequently, the catheter 400 can advance over the wire until the helical anchoring section 408 reaches the skin 414. The catheter 400 can then be rotated until the helical anchoring section 408 is completely under the skin 414. In general, the subcutaneous tissue layer 416 will be thick enough such that the helical anchoring section 408 will not enter the vessel 412. Furthermore, to prevent inadvertent rotations, the catheter 400 can be optionally covered with sterile dressings as necessary.

In some embodiments, the helical configuration can also be used on thoracic catheters or chest tubes, as illustrated in FIGS. 5A and 5B. Referring to FIG. 5A, a thoracic catheter 500 can possess the similar features of the vascular catheter 400 but to be used in a pleural space 504 (i.e., lung) to evacuate air and fluid or on occasion, infuse therapeutic agents. Due to the fact that the tip of the catheter 500 often needs to be precisely positioned at a specific surgical location (e.g. at the thoracic apex), the catheter 500 may possess a particularly long helical anchoring section 502 for gaining access to the desired surgical location across the subcutaneous tissue 506 and the pleural space 504. The insertion process can include firstly creating a small skin incision, followed by creating a tunnel through the subcutaneous tissue 506 and into the pleural space 504, then advance the catheter (generally without a trocar) 500 through the small skin incision, and rotate the catheter 500 until the helical shaped anchoring section 502 can reside completely under the skin 502 and the catheter tip is located at the proper position.

In some embodiments, the self-anchoring feature of the percutaneous catheters may be formed by screw-like threads which engages the skin and prevents dislodgement, as illustrated in FIGS. 6A and 6B. In many ways, this embodiment can be similar to that of the helical configuration. The catheter 600 as shown in FIG. 6A can include a proximal hub 602, a straight proximal section 504, a threaded anchoring section 606 followed by a straight distal section 608. Or as shown in FIG. 6B, the threaded anchoring section 606 can be contiguous with the proximal hub 602, eliminating the straight proximal section 604 of the catheter 600, where the threaded anchoring section 606 can be rigid, semi-rigid or flexible. In some embodiments, the width, pitch and number of turns of the threads can be optimized to facilitate a better engagement with a wide range of skin thicknesses.

It should be appreciated that the threaded anchoring section configuration can be applied to all percutaneous catheters including the peripheral vascular catheters and the central vascular catheters.

For example, FIGS. 7A and 7B are diagrams illustrating a peripheral vascular catheter 700 having a threaded anchoring section 702 in accordance with an embodiment of the present disclosure. Referring to FIG. 7A, the anchoring section 702 can be directly connected to a hub section 704 designed to function as an infusion source or a withdrawal mechanism. The anchoring section 702 can be designed to have threads configured to anchor onto tissues. As shown in FIGS. 7A and 7B and similar to the insertion process illustrated in FIGS. 3A and 3B, after the catheter 700 has been inserted through a layer of tissue 708 (i.e., skin) using an insertion needle 706, the catheter 700 can be rotated to be entered through the opening provided by the insertion needle 706, where the anchoring section 702 can be threaded into the tissue layer 708, thereby providing anchoring to the catheter 700.

Figure 8A:
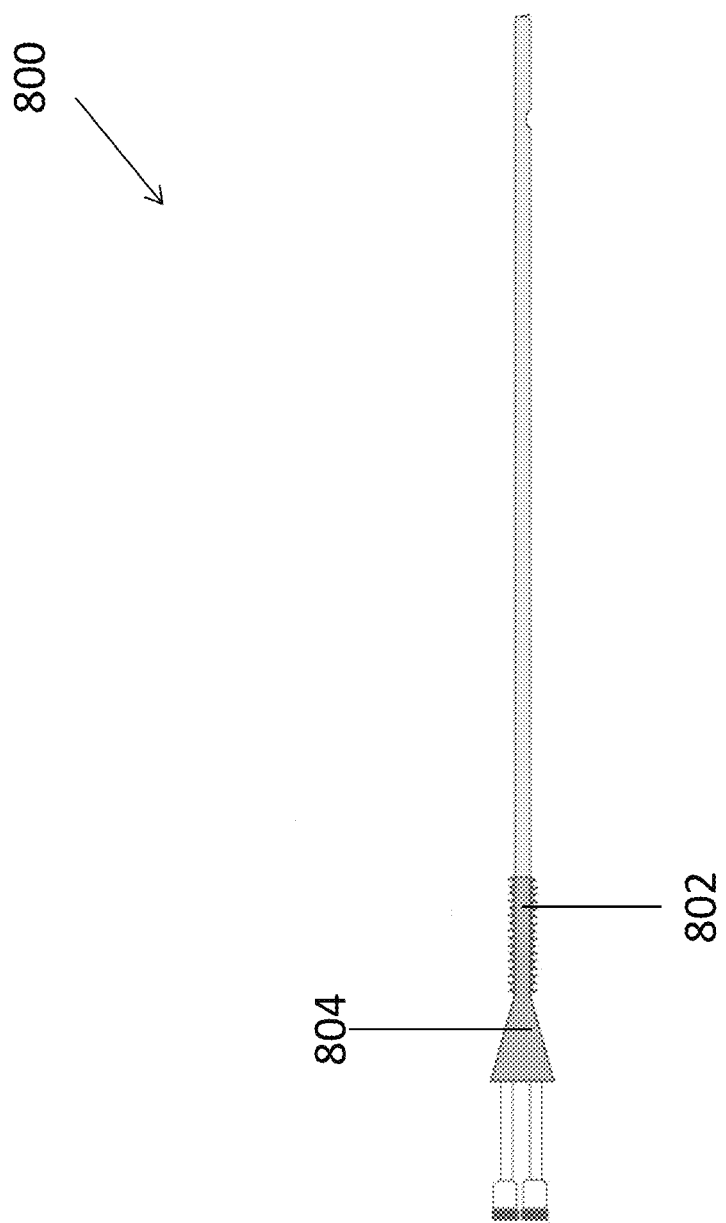
FIG. 8A illustrate a central vascular catheter having a threaded self-anchoring section.
Figure 8B:
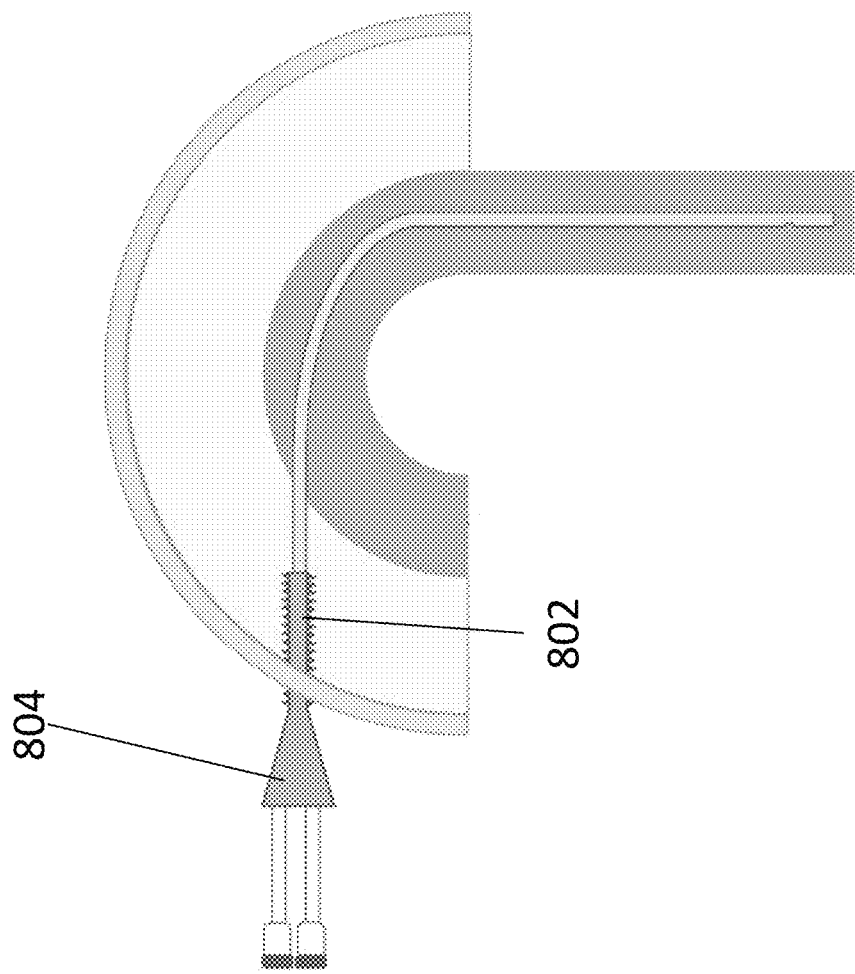
FIG. 8B illustrate a central vascular catheter having a threaded self-anchoring section being inserted into an anatomic structure.

In a similar fashion, central vascular catheters can also be equipped with the threaded anchoring sections designed to provide anchoring within tissues. FIGS. 8A and 8B are diagrams illustrating a central vascular catheter 800 in accordance with embodiments of the present disclosure. Referring to FIGS. 8A and 8B, the catheter 800 can include an anchoring section 802 equipped with threads designed to anchor onto tissues, where the anchoring section 802 can be directly connected to a proximal hub section 804 designed to be coupled to other instruments. In use, after an initial insertion into a tissue, the catheter 800 can be rotated until the threaded anchoring section 802 can be threaded into the tissue, thereby providing anchoring to the catheter 800, as illustrated in FIG. 8B.

It should be appreciated that although described as being helical in design or threaded in design, the self-anchoring portion of the catheter can be one of a helical design, a threaded design, any self-anchoring designs, or a combination thereof.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A method for operating a catheter comprising:
    inserting a catheter into a tissue, the catheter having a substantially straight section, an anchoring section positioned proximal to the substantially straight section, and a pathway extending the length of the catheter, the anchoring section having a curvature for providing longitudinal traction with a tissue to anchor the catheter to the tissue and the pathway mimicking the curvature of the anchoring section; wherein the step of inserting a catheter further comprises coupling an insertion needle to the catheter for piercing the tissue; wherein the step of coupling an insertion needle to the catheter further comprises inserting a rigid portion of the insertion needle through the curvature of the anchoring section;
    advancing the substantially straight section into the tissue;
    advancing the catheter in a rotating fashion, until the anchoring section gains traction with the tissue; and
    anchoring the catheter using the traction created between the anchoring section and the tissue.

2. The method of claim 1, wherein inserting the rigid portion of the insertion needle straightens the anchoring section.

3. The method of claim 1, further comprises removing the insertion needle from the pathway.

4. The method of claim 1, wherein the step of inserting a catheter further comprises pushing the catheter until the substantially straight section reached a desirable anatomic location.

5. The method of claim 1, wherein the step of advancing the catheter further comprises rotating the catheter until the anchoring section is substantially submerged in at least one layer of tissue.

6. A method for operating a catheter comprising:
    providing a catheter having a substantially straight section, an anchoring section positioned proximal to the substantially straight section and a pathway extending the length of the catheter, the anchoring section having a curvature for providing longitudinal traction with a tissue to anchor the catheter to the tissue and the pathway mimicking the curvature of the anchoring section;
    inserting a needle through the curvature of the anchoring section to straighten the anchoring section and through the substantially straight section;
    inserting the substantially straight section of the catheter into a tissue until the anchoring section is near an entry point of the tissue;
    removing the needle from the pathway to return the curvature to the anchoring section;
    advancing the catheter in a rotating fashion, until the anchoring section gains traction with the tissue; and
    anchoring the catheter using the traction created between the anchoring section and the tissue.

7. The method of claim 6, wherein the needle includes a distal tip designed to protrude from a distal end of the catheter and pierce through the tissue.

8. The method of claim 6, wherein the step of inserting a catheter further comprises pushing the catheter until the substantially straight section reached a desirable anatomic location.

9. The method of claim 6, wherein the step of advancing the catheter further comprises rotating the catheter until the anchoring section is substantially submerged in at least one layer of tissue.

10. The method of claim 6, wherein the removing the needle from the pathway comprises removing the needle once at least a substantial portion of the anchoring section is positioned within the tissue.

\* \* \* \* \*